United States Patent [19]
Farin et al.

[11] Patent Number: 5,153,135
[45] Date of Patent: Oct. 6, 1992

[54] PSEUDOMONAS STRAINS CAPABLE OF PRODUCING LIPOLYTIC ENZYMES FOR DETERGENT COMPOSITIONS

[75] Inventors: Farrokh Farin, Hazerwoude-Rijndijk; Johannes Jacobus M. Labout, Heemstede; Gerrit J. Verschoor, Benthuizen, all of Netherlands

[73] Assignee: Gist-Brocades N.V., Delft, Netherlands

[21] Appl. No.: 500,769

[22] Filed: Mar. 28, 1990

Related U.S. Application Data

[62] Division of Ser. No. 34,418, Mar. 6, 1987, Pat. No. 4,933,287.

[30] Foreign Application Priority Data

Aug. 9, 1985 [EP] European Pat. Off. ........ 85-2013028

[51] Int. Cl.⁵ .......................... C12N 1/00; C12N 1/20
[52] U.S. Cl. .................................. 435/253.3; 435/874
[58] Field of Search ................ 435/252.34, 874, 253.3

[56] References Cited

U.S. PATENT DOCUMENTS

| | | | |
|---|---|---|---|
| 3,511,753 | 5/1970 | Prave et al. | 435/198 |
| 3,875,007 | 4/1975 | Kobayashi | 435/198 |
| 4,933,287 | 6/1990 | Farin et al. | 435/198 |
| 4,950,417 | 8/1990 | Bycroft et al. | 435/874 |
| 4,981,611 | 1/1991 | Kolattukudy et al. | 252/174.12 |

*Primary Examiner*—Douglas W. Robinson
*Assistant Examiner*—Susan M. Weber
*Attorney, Agent, or Firm*—Bierman and Muserlian

[57] ABSTRACT

Novel lipolytic enzymes are provided having an optimum pH in the range of 8 and 10.5 which exhibit effective lipase activity in an aqueous solution containing a detergent at a concentration of up to about 10 g/l under washing conditions at a temperature of 60° C. or below and at a pH between 7 and 11. These lipases are useful in washing compositions, premixes and enzymatic detergent additives. They are obtainable from bacteria strains selected from *Pseudomonas pseudoalcaligenes, Pseudomonas stutzeri* and *Acinetobacter calcoaceticus.* Preferred strains are *Ps. pseudoalcaligenes* CBS 467.85, CBS 468.85, CBS 471.85, CBS 473.85 and ATCC 29625, *Ps. stutzeri* CBS 461.85 and *Acinetobacter calcoaceticus* CBS 460.85, and variants and mutants thereof.

4 Claims, No Drawings

PSEUDOMONAS STRAINS CAPABLE OF PRODUCING LIPOLYTIC ENZYMES FOR DETERGENT COMPOSITIONS

PRIOR APPLICATION

This application is a division of U.S. patent application Ser. No. 034,418 filed Mar. 6, 1987, now U.S. Pat. No. 4,933,287.

The present invention relates to enzymes for the enzymatic degradation of fatty materials. More specifically, this invention relates to novel lipolytic enzymes with improved lipolytic activity under washing conditions, which make them particularly suitable for use as detergent additives. The invention is also directed towards a process for preparing the novel lipolytic enzymes, their use as additives for washing compositions and to a washing process using these washing compositions. Furthermore, the invention is directed to detergent composition comprising the novel lipolytic enzymes.

The enzyme of this invention comprises at least one of the multiplicity of lipolytic enzymes produced by certain microorganisms and in particular certain bacteria, which have been found to differ one from the other in physicochemical and enzymatic properties.

A special problem associated with laundry cleaning refers to the removal of stains of a fatty nature. This problem will be aggrevated still further if the trend towards lower washing temperatures persists. At the moment, the fat containing dirt is emulsified and removed as a result of the washing process at high temperature and high alkalinity.

Due to the present trend for energy saving, there is a strong tendency toward the use of relatively low washing temperatures, i.e. around 40° C. or lower. There is therefore a need for lipases, which are effective at the lower washing temperatures, stable in high alkaline detergent solutions and stable under storing conditions in both solid and liquid detergent compositions.

Although the use of lipolytic enzymes in detergent compositions has been known for many years (see e.g. the references mentioned on page 1, lines 36-38 of British Patent Specification No. 1,442,418), they appear to be rather unsatisfactory in practice since they exhibit only a very low cleaning efficiency under washing conditions and they do not meet the present stability requirements. For a comprehensive review article, reference is made to H. Andree et al., J. Appl. Biochem., 2 (1980) 218-229, "Lipases as Detergent Components".

Lipolytic detergent additives are also known from, e.g., British Patent Specification No. 1,293,613 and Canadian Patent No. 835,343.

U.S. Pat. No. 3,950,277 and British Patent Specification No. 1,442,418 disclose lipase enzymes combined with an activator and calcium and/or magnesium ions, respectively, which are utilized to pre-soak soiled fabrics and to remove triglyceride stains and soils from polyester or polyester/cotton fabric blends, respectively. Suitable microbial lipases for use herein (apart from animal and plant derived lipases) are said to be those derived from Pseudomonas, Aspergillus, Pneumococcus, Staphylococcus, and Staphylococcus toxins, Mycobacterium tuberculosis, Mycotorula lipolytica, and Sclerotinia.

British Patent Specification No. 1,372,034 discloses a detergent composition comprising a bacterial lipase produced by *Pseudomonas stutzeri* strain ATCC 19154. Furthermore, it is recommended that the preferred lipolytic enzymes should have a pH optimum between 6 and 10, and should be active in said range, preferably between 7 and 9. Around 1970, this presumed *Pseudomonas stutzeri* strain was reclassified as *Pseudomonas aeruginosa*, as appears for example from the ATCC catalogues.

European Patent Application EP-A-0130064 discloses an enzymatic detergent additive comprising a lipase isolated from *Fusarium oxysporum* with an alleged higher lipolytic cleaning efficiency than conventional lipases.

As a result of extensive research and experimentation it has been surprisingly found that lipase preparations could be obtained by cultivation of suitably selected microorganisms, the lipases being capable of exhibiting lipase activity under modern washing conditions, i.e. they are stable and effective at high detergent concentrations, at high pH and at low washing temperatures.

Accordingly, the invention provides novel lipase preparations which are obtainable by cultivation of certain strains belonging to the species of *Pseudomonas pseudoalcaligenes, Pseudomonas stutzeri* and *Acinetobacter calcoaceticus*. Said lipases possess an pH optimum between about 8 and 10.5, exhibit effective lipase activity in an aqueous solution containing a detergent at concentrations of up to about 10 g/l under washing conditions at a temperature of 60° C. or below, preferably 30°-40° C., and at a pH between about 7 and 11, and preferably between about 9 and 10.5. The pH optimum is determined in a pH-stat under conditions of TLU determination, which is described hereinafter on page 16.

According to a preferred embodiment of the invention, a lipase preparation can be obtained by cultivating, under usual cultivating conditions, a novel isolate of *Ps. pseudoalcaligenes* selected from the group consisting of the strains with the internal numbers Sp 9, IN II-5, Gr VI-15 and M-1, which were deposited on Aug. 8, 1985, with the Centraal Bureau voor Schimmelcultures (CBS) at Baarn, the Netherlands, under numbers CBS 467.85 (7181), CBS 468.85 (7182), CBS 471.85 (7185) and CBS 473.85 (7187), respectively. These isolates are identified by the phenotypic characteristics listed in Table 1.

According to another preferred embodiment of the invention, a lipase preparation can be obtained by cultivating, under usual cultivating conditions, the Type strain of *Ps. pseudoalcaligenes* subspecies *citrulli*, deposited with the American Type Culture Collection under number ATCC 29625.

It is well known to people skilled in the art that *Pseudomonas pseudoalcaligenes* species, exemplified by the strains DSM 50188 (the same as ATCC 17440, Type strain) and DSM 50189, do not produce lipases. However, it is also known that said species is rather heterogenous. This is manifested by the identification of new plantpathogeneic bacteria, discovered by N. W. Schaad et al., Int. J. Syst. Microbiol., 28 (1978) 117-125, and named *Pseudomonas pseudoalcaligenes* subspecies *citrulli*, and by M. Goto, Int. J. Syst. Microbiol., 33 (1983) 539-545, named *Pseudomonas pseudoalcaligenes* subspecies *konjaci*.

Although the phenotypic characteristics of the two subspecies *citrulli* and *konjaci* differ somewhat from each other and from the type strain of the species mentioned above, it is considered by those skilled in the art, that these subspecies belong to the species *Ps. pseudoalcaligenes* (see e.g. N. J. Palleroni, Bergey's Manual of Systematic Bacteriology, vol. 1 ed. N. R. Krieg, Williams and Wilkins, Baltimore/London 1984 p. 173–174). Their existence shows the natural variation found in the phenotypic characteristics of the *Ps. pseudoalcaligenes* species. The variation of the phenotypic characteristics is expressed, among other traits, in the production of lipase by the new subspecies citrulli and konjaci of the *Ps. pseudoalcaligenes* species.

It will also be appreciated by skilled persons, that the new isolates differ somewhat from the described characteristics of the until now discovered subspecies of *Pseudomonas pseudoalcaligenes*, but that they belong to this species anyway.

The lipase produced by each of the 4 selected strains of *Pseudomonas pseudoalcaligenes*, defined above, shows a surprisingly good stability and effectiveness under washing conditions. The same applies to the lipase produced by the Type strain of *Pseudomonas pseudoalcaligenes* subspecies citrulli, indicated above, the useful properties of which could in no way be derived from the reference of Schaad et al.

According to still another preferred embodiment of the invention a lipase preparation can be prepared by cultivating, under usual cultivating conditions, a novel *Pseudomonas stutzeri* strain, which bears the internal number Thai IV 17-1 and which has been deposited with CBS on Aug. 8, 1985 under No. CBS 461.85 (7175). The strain is identified by the phenotypic characteristics listed in Table 2. This *Pseudomonas stutzeri* strain is able to produce a lipase which is stable in washing solutions, containing up to 10 g detergent/l at 35° C. and pH 9.0.

As mentioned above, it was already known that a *Pseudomonas stutzeri* strain, ATCC 19154, was able to produce a stable lipase which can be used in detergents (see also U.S. Pat. No. 3,511,753). However, this deposited strain has been reclassified as *Pseudomonas aeroginosa*, see e.g. ATCC Catalogue of Bacteria, Phages and rDNA Vectors, 16th ed., 1985, p. 134, no. 19154. A skilled person could certainly not predict or expect that authentic *Pseudomonas stutzeri* strains could produce stable lipases as defined in the present invention. *Pseudomonas stutzeri* has been known for a long time as a rather heterogenous species, embracing several bacteria strains, the enzyme producing potential of which were very different. Moreover, no indication was given as to the possibility of using such lipases in modern washing compositions and more particularly, that its stability under the indicated washing conditions would be so good.

According to still a further preferred embodiment of the invention, a lipase preparation can be obtained by cultivating, under usual cultivating conditions, a novel isolated strain of *Acinetobacter calcoaceticus*, which has the internal number Gr V-39 and which is deposited with CBS on Aug. 8, 1985, under No. CBS 460.85 (7174). This strain is identified by the phenotypic characteristics listed in Table 2. The lipase preparation obtained from the deposited strain was stable and effective up to 10 g detergent/l of washing solution at 40°-50° C. and up to pH 10.3.

The preferred lipase preparations of this invention are those which cause a hydrolysis of at least about 10% and preferably at least about 20% of the recovered fats under the conditions described in Example 9 hereinafter for powder detergent at a minimum detergent concentration of 2 g/l.

TABLE 1

Characteristics of *Pseudomonas pseudoalcaligenes* strains Sp 9, IN II-5, Gr VI-15 and M-1

| Character | Strain | | | |
|---|---|---|---|---|
| | Sp 9 | IN II-5 | Gr VI-15 | M-1 |
| Shape and size of cells | rods | rods | rods | rods |
| Polymorphism | absent | absent | absent | absent |
| Motility | motile | motile | motile | motile |
| Formation of spores | none | none | none | none |
| Gram staining | − | − | − | − |
| Oxidase reaction | + | + | + | + |
| Anaerobic dextrose | − | − | − | − |
| Aerobic: | | | | |
| dextrose | − | − | − | − |
| maltose | − | − | − | − |
| sucrose | − | − | − | − |
| D-xylose | − | − | − | + |
| Arginine dihyrolase | + | + | − | + |
| Lysine decarboxylase | − | − | − | − |
| Ornithine decarboxylase | − | − | − | − |
| Urease | − | − | − | − |
| Gelatin hydrolysis | − | − | − | − |
| Catalase | + | + | + | + |
| Beta-galactosidase (ONPG-method) | − | − | − | − |
| Indole formation | − | − | − | − |
| Reduction of nitrate | + | + | + | + |
| Nitrate reduced passed nitrite ($N_2$-gas production) | − | − | − | − |
| Starch hydrolysis | − | − | − | − |
| Phenylalanine deamination | − | − | − | (+) |
| Citrate utilization | + | + | + | + |
| Growth on: | | | | |
| 1% cetrimide | + | − | n.t. | n.t. |
| 6.5% NaCl | − | n.t. | n.t. | n.t. |
| McConkey | + | + | + | + |
| Growth at: | | | | |
| 4° C. | − | − | − | − |
| 42° C. | + | + | + | + |
| Hydrogen sulfide production | − | − | n.t. | n.t. |
| Behaviour towards oxygen | aerobic | aerobic | aerobic | aerobic |
| Nutritive requirements | none | none | none | none |
| Pigment formation on: | | | | |
| King-A medium | − | − | − | − |
| King-B medium | − | − | − | − |
| Source of isolate | soil (Spain) | soil (India) | soil (Greece) | soil (Malaysia) | n.t. = not tested
(+) weak or delayed

TABLE 2

Characteristics of *Pseudomonas stutzeri* strain Thai IV 17-1 and *Acetobacter calcoaceticus* strain Gr V-39

| Character | Strain | |
|---|---|---|
| | Thai IV 17-1 | Gr V-39 |
| Shape and size of cells | rods | rods, but coccoid at stationary phase |
| Polymorphism | absent | absent |
| Motility | motile | non-motile |
| Formation of spores | none | none |
| Gram staining | − | − |
| Oxidase reaction | + | − |
| Anaerobic dextrose | − | + |
| Aerobic | | |
| dextrose | (+) | + |
| maltose | − | − |
| sucrose | − | − |
| D-xylose | n.t. | + |
| Arginine dihydrolase | − | − |
| Lysine decarboxylase | − | − |
| Ornithine decarboxylase | − | − |
| Urease | − | − |

TABLE 2-continued

Characteristics of *Pseudomonas stutzeri* strain Thai IV 17-1 and *Acetobacter calcoaceticus* strain Gr V-39

| Character | Strain Thai IV 17-1 | Strain Gr V-39 |
|---|---|---|
| Gelatin hydrolysis | − | − |
| Catalase | + | + |
| Beta-galactosidase (ONPG-method) | − | − |
| Indole formation | − | − |
| Reduction of nitrate | + | − |
| Nitrate reduced passed nitrite ($N_2$-gas production) | + | − |
| Starch hydrolysis | + | − |
| Phenylalanine deamination | − | − |
| Citrate utilization | + | + |
| Growth on: | | |
| 1% cetrimide | + | n.t. |
| 6.5% NaCl | (+) | n.t. |
| McConkey | + | + |
| Growth at: | | |
| 4° C. | − | − |
| 42° C. | + | + |
| Hydrogen sulfide production | − | n.t. |
| Behaviour towards Oxygen | aerobic | aerobic |
| Nutritive requirements | none | requires nutrients |
| Pigment formation on: | | |
| King-A medium | − | n.t. |
| King-B medium | − | n.t. |
| Source of isolate | soil (Thailand) | soil (Greece) | n.t. = not tested
(−) weak or delayed

According to another aspect of the invention there are provided washing compositions containing a lipase according to the invention together with a detergent and optionally other ingredients which are commonly used in detergent compositions. The ingredients of the detergent compositions of the invention may include, in addition to the essential lipase one or more of the following:

1. surfactants commonly used in enzymatic detergent compositions. Generally, naturally or synthetic surface active compounds may be used, e.g. water-soluble soaps, cationic, anionic, non-ionic, ampholytic or zwitterionic surfactants. An example of a commonly used surfactant of this type is dodecyl benzene sulphonate. Generally the surfactants, which may be used alone or in an admixture, are present in amounts of about 4 to 50% w/w of the washing composition, 2. water softeners such as complex phosphates, e.g. alkali metal tripolyphosphate or an alkali metal pyrophosphate or zeolites, preferably in amounts of up to 40% by weight of the washing composition. Furthermore or alternatively compounds such as alkali metal cyano-triacetate or alkali metal citrate may be included, showing a complex action in washing compositions, 3. alkali metal silicate or weakly alkaline compounds such as alkali metal bicarbonate, usually up to 20% by weight, 4. fillers, such as alkali metal sulphate, 5. compounds, such as carboxymethylcellulose, perfumes, optical brighteners, buffering compounds, polyalkylene glycols or ethanol, 6. other types of enzymes such as proteases and amylases.

In the enzymatic washing composition according to the invention, the lipase activity is preferably in the range of from 1 to 20,000 TLU/g of composition, while the proteolytic enzyme activity is preferably in the range from 50–10,000 Delft Units/g of washing composition. One TLU (True Lipase Unit) is defined as the titratable fatty acids equivalent to the amount of 1 umole NaOH per minute (see also page 16 hereinafter). The Delft Units are defined in J. Amer. Oil Chem. Soc. 60 (1983), 1672.

Another group of compounds which can be incorporated in the washing compositions according to the invention are bleaching agents such as alkali metal perborate, especially sodium perborate, alkali metal percarbonate, such as sodium percarbonate, peracids and salts thereof, and activators for these bleaching agents such as TAED. When the washing composition contains perborates, percarbonates, activators and optical brighteners on the one hand and proteases on the other hand, it is highly surprising that the lipase preparations of the present invention continue to exhibit their high stability in the presence of these ingredients.

The washing compositions of the invention may be prepared in the usual manner, for example by mixing together the components or by the preparation of an initial premix, which is subsequently finished by mixing with the other ingredients. According to one possible preparation route, one or more lipase preparations are mixed with one or more of the other compounds to make a concentrate of a predetermined enzymatic activity, which concentrate can then be mixed with the other desired components.

According to a particularly preferred embodiment, the lipolytic enzymes of the invention are in the form of an enzymatic detergent additive. This additive may also contain one or more other enzymes, for example a protease and/or an amylase, which can be used in modern washing compositions, and one or more other components, which are commonly used in the art, for example a non-ionic, salt, stabilising agent and/or coating agent. Preferably, the enzymatic detergent additive comprises besides a lipase of the invention a protease and optionally an alpha-amylase. It has been found that proteolytic enzymes do not break down the the lipolytic enzymes of the invention. The enzymatic detergent additives according to the invention are generally mixed with oils or more detergents and other components known in the art to form washing compositions.

According to a specific embodiment, an enzymatic detergent additive is used, wherein the lipase activity is in the range of from $10^2$ to $10^6$ TLU/g of additive, while the optionally present proteolytic activity is in the range of from $5 \times 10^4$ to $10^6$ Delft Units/g.

The enzymatic detergent additives of the invention may be in the form of, for example, granulates or prills, prepared according to methods which are generally known in this specific area of the art. See e.g. British Patents 1,324,116 and 1,362,365 and U.S. Pat. Nos. 3,519,570, 4,106,991 and 4,242,219.

In a specific embodiment of the invention, the enzymatic detergent additive is provided in liquid form with an enzyme stabilizer. This stabilizer is e.g. propylene glycol. Such liquid additives are preferably used in liquid detergent compositions.

The stable and effective lipase preparations of the present invention can be suitably prepared by cultivating the microorganisms defined hereinbefore under appropriate conditions. In order to obtain high yields of enzyme, media containing readily assimilable carbon and energy sources are necessary, as is a nitrogen source of organic origin such as casein. More preferably, a fat or oil is added to the culture medium as well as calcium and magnesium salts and trace elements.

According to a preferred embodiment of the invention the cultivation process is carried out in skim milk, previously diluted with water in a ratio of from 1:1 up to 1:25 w/v. Good aeration is necessary during fermentation. The pH of the medium is suitably kept between 6 and 10 and preferably between 6.5 to 9.

The invention provides further a washing process, using a detergent composition of the invention. Such a process may be satisfactorily carried out at a temperature of about 60° C. or below and preferably at 30°-40° C., at a pH usually between 7 and 11. The washing time is generally between 10 and 60 min. More preferably for the washing process, a washing solution is used, containing the detergent composition of the present invention in an amount in the range of from 0.5 to 15 g per liter of washing solution, preferably 1-10 g/l.

Performance of lipases in the washing process

Modern detergent compositions contain ingredients chosen for optimum efficacy in the washing process. It is self-evident that if a lipase is to be used in a modern washing process, it should be compatible with the usual active and effective ingredients found in the modern detergent formulations. To this end a number of test criteria has been chosen which may be used for the demonstration of the activity and effectiveness of the lipases of the invention, under washing conditions. These criteria are:

1. Activity of lipases in the presence of a widely used detergent builder such as sodium tripolyphosphate (TPP). This criterium is significant, since it is a widely held belief that lipases are dependent on alkali metal ions such as calcium for their activity and stability. Such calcium dependent lipases would thus not be suitable for use in modern washing processes.

2. Activity of lipases in modern detergent solutions. There are numerous modern detergent compositions which may be used for testing the activity and effectiveness of alkaline lipases. We have chosen to use, among others, a powder detergent composition and a liquid formulation as typical examples of widely used modern detergent formulations. These typical modern detergent compositions are:

ALL® (powder), a product from Unilever, The Netherlands. In our tests we used ALL-base (obtained from Unilever Research, Vlaardingen, The Netherlands) which is the same formulation as ALL, without perborate, bleach activator (TAED) and enzymes. ALL is a Registered Trade Mark.

TIDE® (liquid), a product from Procter & Gamble and commercially available in the USA. For our tests, the enzymes present in this formulation were inactivated by heat treatment. TIDE is a Registered Trade Mark.

3. Activity of lipases in ALL including proteases. As proteases are an important ingredient of modern detergent compositions, the activity and effectiveness of lipases should be manifest in the presence of this detergent ingredient (together with the surfactant matrix).

4. Activity of lipases in the presence of a typical bleaching agent (such as perborate) and a bleaching activator (such as TAED). Bleaching agents (and their activators at lower washing temperatures) are important ingredients of some modern detergent compositions. Activity and effectiveness of lipases in their presence are considered a significant criterium.

In order to evaluate the contribution of the lipases of the invention to the removal of oils and fats from textiles, an appropriate test system is necessary which allows an unequivocal determination of the activity of the lipases of the invention in washing solutions.

The test-fabrics commonly used, such as EMPA 101 and EMPA 102 (commercially obtainable from Eidgenössische Materialprüfungs and Versuchsanstalt, St. Gallen, Switzerland) have the drawback that detergency is measured as removal of pigment. Whether the removal of pigment from EMPA 101 and 102 fabrics may be directly correlated to the removal of fats or fatty acids is a pertinent question and for this reason alone these fabrics are not considered to be relevant for the evaluation of lipase performance.

Other test systems, for example as described in EP-A-0130064, also rely on the removal of dye from an artificially soiled fabric. The same objection made to the use of EMPA 101 and EMPA 102 test fabrics does also apply here. Moreover, in the test system of the above-mentioned patent application, emulsified fat is used as a substrate for alkaline lipases. This type of fat does not correspond with most of the fat stains which have to be tackled by a modern washing solution, in that such stains are not in emulsified form and non-emulsified fat as such is in contact with the fabric.

The test system described by Andree et al., J. Appl. Biochem., 2 (1980) 218-229, uses radioactively labelled fat deposited on the fabric. After the wash process the radioactivity on the fabric swatch is measured and related to lipolytic activity. In this system, however, it is not possible to distinguish between the radioactivity due to fat and that due to fatty acids and therefore this test system is not a reliable measure of the performance of alkaline lipases in the washing process.

For the purpose of this invention a new test has been developed, hereinafter called SLM-test, which is used for the evaluation of alkaline lipases and their activity and effectiveness in the washing process. The SLM-test uses the same principles as the method developed by T. Hashimoto et al., Yukagaku 34 (1985), 606-612, but the time necessary for the analysis has been drastically reduced. The method includes using immobilized, non-emulsified fat or oil on a fabric as the test stain, extracting the swatch after the washing process and analysing the extracts for fats and fatty acids. Depending on the conditions used, fatty acids, formed as a result of lipase activity, together with residual triglycerides may stay on the textile during the washing process. Therefore, the quantities of the products left on the swatch appear to be a good measure of the performance of lipases during the washing process. The SLM-test will be disclosed in more detail hereinafter, under the general methods of analysis.

The invention is further illustrated by the following Examples. In the Examples the general methods of analysis were conducted as follows.

Assay for the determination of lipase activity

A. Olive oil hydrolysis (TLU method)

Activities of the lipase preparations of the invention were determined either based on the hydrolysis of olive oil or of p-nitrophenyl-laurate. The former method is essentially according to Näher (G. Näher (1974) in:

"Methods of Enzymatic Analysis", Vol. II, pp. 814-818, H. U. Bergmeyer, ed., Academic Press, N.Y., London) except that the fatty acid liberated was measured at pH 8.0 and 25° C. in a pH-stat. One True Lipase Unit (TLU) is defined as the titratable fatty acids equivalent to the amount of 1 μmole NaOH per minute.

B. p-Nitrophenyl laurate hydrolysis (NPL method)

The method based on the hydrolysis of p-nitrophenyl laurate to p-nitrophenol and lauric acid is essentially as follows: an appropriate amount of lipase is diluted in 0.05M MOPS (3-N-Morpholine propane sulfonic acid)-NaOH, pH 8.0 to about 0.003-0.008 Units NPL/ml. One NPL Unit is defined as the amount of lipase necessary to release one μmole of p-nitrophenol. 4 ml of the lipase solution are mixed with 1 ml p-nitrophenyl laurate solution (25 mg p-nitrophenyl laurate in 25 ml ethanol and two drops of 1N HCl) and incubated for 10 min at 30° C. The reaction is stopped by the addition of 5 ml alcoholic-Tris solution (2.5 g Tris-(hydroxymethyl-aminomethane) in 1 l ethanol) and cooled to room temperature. Absorbance is read at 400 nm and corrected for the absorbance of an incubation without lipase. The amount of μmoles p-nitrophenol released is calculated from a calibration curve constructed with the absorbance values at 400 nm of appropriate solutions of p-nitrophenol in ethanol, 1 ml of which is added to 4 ml 0.05M MOPS-NaOH buffer, pH 8.0, and 5 ml alcoholic-Tris solution.

The stability of the lipases was followed in the time by measuring the activities at 0, 15 and 30 minutes (sometimes up to 90 minutes) with one of these methods.

Assay for the determination of lipase stability in washing solutions

In order to evaluate the stability of a number of lipases according to the invention in washing solutions the following experiments were set up.

A proper amount of a lipase preparation, obtained as described in Example 1, was brought in a solution of:

a) Synthetic Tap Water (STW) containing 0.433 g $CaCl_2.6aq$, 0.140 g $MgCl_2.6aq$ and 0.210 g $NaHCO_3$ per litre of distilled water, b) a detergent selected from: p1 ALL-base (=ALL without perborate, TAED and enzymes)

TIDE plus (=TIDE containing sodium tripolyphosphate)

TIDE minus (phosphate free, containing other builder)

ALL-base was obtained from Unilever Research, The Netherlands. TIDE plus and TIDE minus are commercially available from Procter and Gamble, USA. ALL and TIDE are Registered Trade Marks.

The experiments were carried out at pH 9.0 or 10.3 at 35°, 40° or 50° C. Samples were taken from the mixtures at 0, 15 and 30 minutes (sometimes up to 90 minutes), and residual lipase activity was determined with either of the methods described. The lipases used were *Pseudomonas pseudoalcaligenes* strains Sp 9 (CBS 467.85), IN II-5 (CBS 468.85), Gr VI-15 (CBS 471.85) and M-1 (CBS 473.85), *Pseudomonas stutseri* strain Thai IV 17-1 (CBS 461.85) and *Acetobacter calcoaceticus* strain Gr V-39 (CBS 460.85).

The results are shown in Examples 4-8.

Assay for the determination of the lipase performance under washing conditions (SLM-test)

The following is a typical Example of how the SLM-test is preferably carried out.

EMPA 211 cotton swatches are used as the fabric and triolein or purified olive oil (both products of Sigma (USA)) as the substrates. The hydrolysis of triolein can be followed by chromatographic methods after extraction of the textile.

The washing procedure preferably employed for the purpose of the SLM-test is as follows:

A volume of 20 μl containing 5 mg olive oil dissolved in acetone (25%) is spotted on a cotton Swatch (3×3 cm). The swatch is air dried at room temperature. The washing solution consisting of 10 ml of STW (Standard Tap Water: 0.433 g $CaCl_2$, 0.140 g $MgCl_2.6$ aq and 0.210 g $NaHCO_3$ per liter of distilled water) or detergent dissolved in STW is placed in an Erlenmeyer flask (25 ml) with a ground stopper and kept in a shaking water-bath at 40° C. The washing process is started by adding lipase (20 TLU, see hereinafter) and immediately thereafter the soiled swatch, to the Erlenmeyer flask and shaking for 40 min at 40° C. In a blank experiment no lipase is added.

After washing, the swatch is rinsed with STW and subsequently dried at room temperature. The dried swatches are extracted by rotation in a glass tube containing 5 ml of solvent having the same composition as the eluent used for the chromatographic separation of substrate and products.

In the extraction solution the residual triglyceride and the free fatty acid formed are determined by HPLC.

| Equipment and conditions: | |
| --- | --- |
| Pump: | Model 2150 (LKB) |
| Detection: | Refractive index monitor (Jobin Jvon). |
| Injection system: | Wisp (MILLIPORE): 10 μl. |
| Integrator: | SP 4270 (Spectra Physics) |
| Column: | CP Microspher-Si (CHROMPACK), 100 × 4.6 mm. |
| Eluent: | n-Hexane/isopropylalcohol/formic acid: 975:25:2.5 (v/v), 1 ml/min. |
| Temperature: | ambient |

Under these conditions the retention times of triolein and oleic acid are 1.2 and 1.6 min respectively. The peak area or peak height are measured. They are a measure of the recovery of the triglyceride and fatty acid after extraction from the swatch. The recovery of triglyceride after extraction from the unwashed swatch is taken as 100%.

Under the conditions described above the ratio of the refractive index responses between olive oil and oleic acid was found to be 0.85 on the basis of peak area and 1.1 on the basis of peak height.

EXAMPLE 1

Preparation of freeze-dried supernatant of a lipase fermentation of strain Sp 9

*Pseudomonas pseudoalcaligenes* strain Sp 9 (CBS 467.85) was inoculated in 30 ml sterile brain-heart infusion (BHI) medium (Difco) in a 100 ml conical flask. The culture was shaken for 16 hours at 30° C. in an orbital shaker at 300 rpm. The BHI grown cells were inoculated into a 2 l. conical flask, containing 500 ml of sterile skim milk medium. The skim milk medium was prepared as follows:

100 g skim milk (Difco);
   deionized water added to 1 liter;
   the pH is adjusted to 7.0 prior to sterilization;
   sterilization conditions: 110° C. for 30 minutes.

The inoculated skim milk shake flask was shaken for 48 hours in an orbital shaker at 250-300 rpm. The growth temperature for lipase production was 20° C. The broth was centrifuged with a Sorvall R GSA rotor at 10.000 g. at 8°-10° C. The supernatant obtained after centrifugation was then freeze-dried to give a lipase preparation.

The fermentation of other lipase producing strains, for example strains CBS Nos. 460.85, 461.85, 468.85, 471.85, and 473.85, ATCC No. 29625 and DSM No. 2672 (EP-A-130064) were carried out in a similar way, except that for strain CBS 468.85 the growth temperature was 30° C.

The lipase preparations obtained according to this Example were used for the stability experiments described in Examples 4-8.

EXAMPLE 2

Preparation of freeze-dried supernatant of a lipase fermentation of strain Thai IV 17-1

*Pseudomonas stutzeri* strain Thai IV 17-1 (CBS 461.85) was inoculated in 30 ml sterile BHI medium in a 100 ml conical flask. The culture was shaken for 16 hours at 30° C. in an orbital shaker at 300 rpm. The BHI grown cells were inoculated into a 2 l conical flask containing 500 ml of sterile GSM medium. The GSM medium was prepared as follows:

100 g skim milk (Difco or Oxoid);
   deionized water added to 1 l;
   The pH was adjusted to 7.8 by addition of 4N NaOH;
   The temperature was brought to 40° C., with stirring;
   MAXATASE ® (Gist-brocades) solution was then added;
   The temperature and pH were controlled for 1 hour. Then the pH was brought to 7. Sterilization was carried out at 110° C. for 30 minutes.

The MAXATASE solution was prepared as follows:

To 1 g MAXATASE powder ($2.372 \times 10^6$ Delft Units/g) deionized water was added to 25 ml. It was shaken well for 5-10 minutes. The insolubles were removed by centrifugation at 10,000 rpm in the SS34 rotor of a Sorvall centrifuge. The supernatant was filtered through a 0.22u MILLIPORE ® filter. The filtrate was then added per liter of 10% skim milk. The inoculated skim milk was shaken in shake flasks for 48 hours at 20° C. in an orbital shaker at 250-300 rpm. Then the broth was centrifuged in a Sorvall GSA rotor at 10,000 g at 8°-10° C. The supernatant obtained was dialysed in EDTA-treated dialysis tubing against 50 volumes of 10 mM Tris-HCl buffer, pH 8, at 4° C., with 2 changes of buffer, over 24 hours. After dialysis the contents of the dialysis sacs were pooled and then freeze-dried.

In a similar way fermentations were carried out with all other strains mentioned in Example 1, except strain CBS 473.85. The lipase containing supernatants obtained according to this Example (except the lipase from strain M-1) were used for the experiments described in Examples 9 and 10.

EXAMPLE 3

Preparation of freeze-dried supernatant of a lipase fermentation of strain M-1

*Pseudomonas pseudoalcaligenes* strain M-1 (CBS 473.85) was inoculated in 500 ml sterile brainheart infusion (BHI) medium (Difco) in a 500 ml conical flask. The culture was shaken for 18 hours at 30° C. in an orbital shaker at 280 rpm. The BHI grown cells were inoculated in a 20 l fermentor containing 10 l of sterile medium 1 or medium 2.

Medium 1 was prepared as follows:

Suspend 1000 g skim milk in demineralized water till 9.5 l; bring the temperature at 30° C. and the pH at 7.8 with sodium hydroxide solution; add $33 \times 10^6$ ADU ($= 26 \times 10^6$ DU) MAXACAL ® (Dist-brocades) for protease treatment (30° C. and pH 7.0-7.8) during 1 hour. Autoclavation after adding 0.5-10 ml antifoam (SAG 471 or Pluronic L-81): 30 min. at 110° C.

Medium 2 was prepared as follows:

Suspend 400 g casein in 5 l demineralized water; bring the pH at 9.0 (with a solution of sodium hydroxide) and the temperature at 50° C.; add $5 \times 10^7$ ADU ($= 4 \times 10^7$ DU) Maxacal ® for protease treatment; incubation (90 min. at 50° C. and pH=9.0) is stopped by fast heating (incubation 5 min at 90° C.). After cooling to 25° C. adjust the pH to 7.0 by sulfuric acid addition.

The other components (butter 50 g; MgSO$_4$.7aq 5 g; MnSO$_4$.4aq 0.1 g and antifoam SAG 471 0.5-10 ml) were added and the medium filled up till 10 l with demineralized water and autoclaved: 65 min. at 120° C.

The medium was cooled to fermentation temperature (30° C.). Fermentation conditions:

| airflow: | 0.167 vvm |
| stirring: | 1000 rpm |
| pH: | 6.5-10.0 (pref. 6.8-8.0) |

The fermentation was continued for between 35-72 hours.

The broth was centrifuged after fermentation on a Hettich centrifuge (4000 g. 8°-10° C.) for 30 min. The supernatant was cooled to 0° C. and solid (NH$_4$)$_2$SO$_4$ was added to a concentration of 70% (w/w), under stirring. The precipitate formed was separated from the supernatant by centrifugation on a Sorvall centrifuge (10.000 g, 4°-5° C.) for 20-25 min. The precipitate was taken up in a 10 mM Tris HCl buffer (pH 8) of 0° C. and cooled acetone ($< -7°$ C.) was added within 20 min. to a concentration of 65% (w/w). After centrifugation the precipitate was taken up in 10 mM Tris HCl buffer pH 8 and dialysed against 50 volumes of the same buffer at 4° C. with 2 changes of buffer over 24 hours. After dialysis the material was lyophilized and the activity obtained was 6000 TLU/g.

In a similar way all other strains, mentioned in Example 1 can be used, however with the following slight modifications: for strain Sp 9 only medium 1 can be used; the fermentation temperature is 20° C. for all other strains, except for strain IN II-5 which is 20° or 30° C.

EXAMPLE 4

Stability experiments with Pseudomonas pseudoalcaligenes lipases at 8 g ALL-base/l at 35°, 40° and 50° C.

| Source: | freeze-dried supernatant |
|---|---|
| Detergent solution: | ALL-base, 8 g/l |
| pH: | as indicated | a. Temperature: 35° C.

| Lipase strain | pH | NPL/l × $10^{-3}$ | time (min) | residual activity (%) |
|---|---|---|---|---|
| Sp 9 | 9 | 19 | 0 | 100 |
| | | | 15 | 104 |
| | | | 30 | 106 |
| Sp 9 | 10.3 | 19 | 0 | 100 |
| | | | 15 | 88 |
| | | | 30 | 81 |
| IN II-5 | 9 | 11 | 0 | 100 |
| | | | 15 | 107 |
| | | | 30 | 102 |
| IN II-5 | 10.3 | 11 | 0 | 100 |
| | | | 15 | 87 |
| | | | 30 | 77 | b. Temperature: 40° C.

| Lipase strain | pH | TLU/l or NPL/l × $10^{-3}$ | time (min) | residual activity (%) |
|---|---|---|---|---|
| Sp 9 | 9.0 | 14 | 0 | 100 |
| | | | 15 | 102 |
| | | | 30 | 99 |
| Sp 9 | 10.3 | 14 | 0 | 100 |
| | | | 15 | 93 |
| | | | 30 | 83 |
| IN II-5 | 9.0 | 22 | 0 | 100 |
| | | | 15 | 89 |
| | | | 30 | 79 |
| IN II-5 | 10.3 | 22 | 0 | 100 |
| | | | 15 | 76 |
| | | | 30 | 57 |
| Gr VI-15 | 10.3 | 5 | 0 | 100 |
| | | | 15 | 74 |
| | | | 30 | 61 |
| M-1 | 10.3 | 2.8 | 0 | 100 |
| | | | 15 | 63 |
| | | | 30 | 68 | c. Temperature: 50° C.

| Lipase strain | pH | NPL/l × $10^{-3}$ | time (min) | residual activity (%) |
|---|---|---|---|---|
| Sp 9 | 9.0 | 14 | 0 | 100 |
| | | | 15 | 95 |
| | | | 30 | 80 |
| Sp 9 | 10.3 | 14 | 0 | 100 |
| | | | 15 | 56 |
| | | | 30 | 32 |
| IN II-5 | 9.0 | 22 | 0 | 100 |
| | | | 15 | 60 |
| | | | 30 | 49 |
| IN II-5 | 10.3 | 22 | 0 | 100 |
| | | | 15 | 27 |
| | | | 30 | 12 |
| Gr VI-15 | 10.3 | 20.9 | 0 | 100 |
| | | | 15 | 43 |
| | | | 30 | 12 |
| M-1 | 10.3 | 25 | 0 | 100 |
| | | | 15 | 62 |
| | | | 30 | 54 |

EXAMPLE 5

Stability experiments with certain Pseudomonas pseudoalcaligenes lipases at 4 g ALL-base/l at 40° and 50° C.

a.

| Source: | freeze-dried supernatant |
|---|---|
| Detergent solution: | ALL-base, 4 g/l |
| pH: | as indicated |
| Temperature: | 40° C. |

| Lipase strain | pH | NPL/l × $10^{-3}$ | time (min) | residual activity (%) |
|---|---|---|---|---|
| Sp 9 | 9.0 | 14 | 0 | 100 |
| | | | 15 | 102 |
| | | | 30 | 102 |
| Sp 9 | 10.3 | 14 | 0 | 100 |
| | | | 15 | 109 |
| | | | 30 | 98 |
| IN II-5 | 9.0 | 22 | 0 | 100 |
| | | | 15 | 100 |
| | | | 30 | 99 |
| IN II-5 | 10.3 | 22 | 0 | 100 |
| | | | 15 | 96 |
| | | | 30 | 82 | b.

| Source: | Freeze dried supernatant |
|---|---|
| Detergent solution: | ALL-base, 4 g/l |
| pH: | as indicated |
| Temperature: | 50° C. |

| Lipase strain | pH | NPL/l × $10^{-3}$ | time (min) | residual activity (%) |
|---|---|---|---|---|
| Sp 9 | 9.0 | 14 | 0 | 100 |
| | | | 15 | 97 |
| | | | 30 | 92 |
| Sp 9 | 10.3 | 14 | 0 | 100 |
| | | | 15 | 77 |
| | | | 30 | 62 |
| IN II-5 | 9.0 | 22 | 0 | 100 |
| | | | 15 | 100 |
| | | | 30 | 88 |
| IN II-5 | 10.3 | 22 | 0 | 100 |
| | | | 15 | 60 |
| | | | 30 | 47 |

Example 6

Stability Experiments with Pseudomonas Pseudoalcaligenes Strain Sp 9 at 6 g Tide/l at 40° and 50° C.

| Source: | freeze-dried supernatant of Sp 9 |
|---|---|
| Detergent solution: | as indicated, 6 g/l |
| pH: | as indicated | a. Temperature: 40° C.

| Detergent | pH | NPL/l × $10^{-3}$ | time (min) | residual activity (%) |
|---|---|---|---|---|
| TIDE minus | 9.0 | 14 | 0 | 100 |
| | | | 15 | 118 |
| | | | 30 | 115 |
| TIDE minus | 10.3 | 14 | 0 | 100 |
| | | | 15 | 106 |
| | | | 30 | 107 |
| TIDE plus | 9.0 | 14 | 0 | 100 |
| | | | 15 | 129 |
| | | | 30 | 127 |
| TIDE plus | 10.3 | 14 | 0 | 100 |
| | | | 15 | 118 |
| | | | 30 | 105 | b. Temperature: 50° C.

| Detergent | pH | NPL/l × $10^{-3}$ | time (min) | residual activity (%) |
|---|---|---|---|---|
| TIDE minus | 9.0 | 14 | 0 | 100 |
| | | | 15 | 107 |
| | | | 30 | 107 |
| TIDE minus | 10.3 | 14 | 0 | 100 |
| | | | 15 | 79 |
| | | | 30 | 67 |
| TIDE plus | 9.0 | 14 | 0 | 100 |
| | | | 15 | 120 |
| | | | 30 | 127 |
| TIDE plus | 10.3 | 14 | 0 | 100 |
| | | | 15 | 81 |

-continued

| Source: | freeze-dried supernatant of Sp 9 | | |
|---|---|---|---|
| Detergent solution: | as indicated. 6 g/l | | |
| pH: | as indicated | | |
| Detergent | pH | NPL/l × 10⁻³ | time (min) | residual activity (%) |
| | | | 30 | 54 |

Example 7

Stability Experiments of Pseudomonas Stutzeri Lipase Thai IV 17-1 at 5 g All-Base/l at 40° C.

| Source: | freeze dried supernatant of Thai IV 17-1 |
|---|---|
| Detergent solution: | ALL-base. 5 g/l |
| pH: | 9.0 |
| Temperature: | 40° C. |
| Time (min) | resid. act (%) |
| 0 | 100 |
| 25 | 109 |

Example 8

Stability Experiments with Acinetobacter Calcoaceticus Lipase at 8 g All-Base/l at 40° and 50° C.

| Source: | freeze-dried supernatant of Gr V-39 (CBS 460.85) |
|---|---|
| Detergent solution: | ALL-base. 8 g/l |
| pH: | 10.3 |

| a. Temperature: 40° C. | | |
|---|---|---|
| TLU/l × 10⁻³ | time (min) | residual activity (%) |
| 4.0 | 0 | 100 |
| | 15 | 100 |
| | 30 | 80 |

| b. Temperature: 50° C. | | |
|---|---|---|
| NPL/l × 10⁻³ | time (min) | residual activity (%) |
| 23.6 | 0 | 100 |
| | 15 | 27 |
| | 30 | 5 |

EXAMPLE 9

This Example illustrates the performance of lipase strains *Ps. pseudoalcaligenes* Sp 9, IN II-5, Gr VI-15, M-1, ATCC 29625, *Ps. stutzeri* Thai II-5 and *Acetobacter calcoaceticus* Gr V-39 in a washing process according to the SLM-test, where the compatibility of these enzymes with a builder component present in modern washing compositions (TPP), a powder detergent composition (ALL-base) and a liquid formulation (TIDE liquid) was checked.

The SLM-test was carried out as described on pages 18–19 of this specification. Preliminary experiments showed that, under the conditions used, a considerable amount of fatty acids formed by lipase, together with residual triglyceride stayed on the textile during the washing process.

The performance of the lipases mentioned above and the blank was tested by the SLM-method under the following conditions:

standard tap water (STW) adjusted to pH 9.1 with alkali.
sodium tripolyphosphate (TPP): 2 and 10 g/l (pH 9.1).
liquid TIDE: 2 and 4 g/l (pH 7.5)
ALL-base: 2, 4 and 8 g/l (pH 9.2–9.6)

The lipase activity units added (20 TLU) were obtained from the freeze-dried samples produced according to Example 2 and in case of strain M-1 to Example 3. They were found to be as follows:

| Strain | Sp 9 | IN II-5 | Gr VI-15 | M-1 | ATCC 29625 |
|---|---|---|---|---|---|
| Activ. (TLU/g) | 70 | 130 | 50 | 6000 | 35 |
| Strain | Thai IV 17-1 | | Gr V-39 | | |
| Activ. (TLU/g) | 165 | | 62.5 | | |

The results are shown in the following tables.

| Condition | (g/l) | Recovery (%) | | |
|---|---|---|---|---|
| | | Triglycerides | Free fatty acids | Total |
| A. Alkaline lipase: none (blank) | | | | |
| STW | — | 92.7 | | |
| TPP | 2 | 80.6 | | |
| TPP | 10 | 85.0 | | |
| Liquid TIDE | 2 | 63.5 | | |
| Liquid TIDE | 4 | 63.9 | | |
| ALL-base | 2 | 65.3 | | |
| ALL-base | 4 | 65.8 | | |
| ALL-base | 8 | 63.4 | | |
| B. Alkaline lipase from strain Sp 9 | | | | |
| STW | — | 9.4 | 91.0 | 100.4 |
| TPP | 2 | 32.3 | 45.4 | 77.7 |
| TPP | 10 | 34.4 | 19.3 | 53.7 |
| Liquid TIDE | 2 | 23.1 | 25.3 | 48.4 |
| Liquid TIDE | 4 | 29.4 | 20.2 | 49.6 |
| ALL base | 2 | 24.1 | 30.4 | 54.5 |
| ALL base | 4 | 34.6 | 21.3 | 55.9 |
| C. Alkaline lipase from strain IN II-5 | | | | |
| STW | — | 20.4 | 68.3 | 88.6 |
| TPP | 2 | 11.6 | 61.0 | 72.6 |
| TPP | 10 | 39.3 | 6.3 | 45.6 |
| Liquid TIDE | 2 | 35.6 | 16.0 | 51.6 |
| Liquid TIDE | 4 | 37.8 | 13.3 | 51.1 |
| ALL base | 2 | 6.1 | 66.4 | 72.6 |
| ALL base | 4 | 20.6 | 30.6 | 51.2 |
| ALL base | 8 | 44.1 | 11.0 | 55.2 |
| D. Alkaline lipase from strain M-1 | | | | |
| STW | — | 9.3 | 75.9 | 85.2 |
| TPP | 2 | 24.7 | 38.8 | 63.5 |
| TPP | 10 | 32.8 | 9.9 | 42.7 |
| Liquid TIDE | 2 | 33.3 | 12.0 | 45.3 |
| Liquid TIDE | 4 | 37.5 | 16.4 | 53.9 |
| ALL-base | 2 | 12.6 | 37.3 | 49.9 |
| ALL-base | 4 | 29.1 | 15.7 | 44.8 |
| E. Alkaline lipase from strain Gr VI-15 | | | | |
| STW | — | 22.0 | 59.3 | 81.3 |
| TPP | 2 | 24.1 | 48.5 | 72.6 |
| TPP | 10 | 31.5 | 28.1 | 59.6 |
| Liquid TIDE | 2 | 49.3 | 9.5 | 58.8 |
| Liquid TIDE | 4 | 54.4 | 0.0 | 54.4 |
| ALL-base | 2 | 32.0 | 23.0 | 55.0 |
| ALL-base | 4 | 37.3 | 15.6 | 52.9 |
| F. Alkaline lipase from strain ATCC 29625 (Citrulli) | | | | |
| STW | — | 2.8 | 102.5 | 105.3 |
| TPP | 2 | 3.8 | 89.0 | 92.9 |
| TPP | 10 | 42.9 | 13.0 | 55.9 |
| Liquid TIDE | 2 | 10.9 | 54.9 | 65.8 |
| Liquid TIDE | 4 | 19.2 | 27.2 | 46.4 |
| ALL-base | 2 | 24.7 | 40.5 | 65.2 |
| ALL-base | 4 | 36.2 | 20.0 | 56.2 |
| G. Alkaline lipase from Thai IV-17-1 | | | | |
| STW | — | 4.3 | 75.3 | 79.6 |
| TPP | 2 | 24.7 | 29.9 | 54.7 |

| | | Recovery (%) | | |
|---|---|---|---|---|
| Condition | (g/l) | Triglycerides | Free fatty acids | Total |
| TPP | 10 | 44.6 | 10.1 | 54.8 |
| Liquid TIDE | 2 | 21.2 | 29.3 | 50.5 |
| Liquid TIDE | 4 | 24.6 | 17.9 | 42.6 |
| ALL-base | 2 | 23.9 | 27.2 | 51.2 |
| ALL-base | 4 | 47.0 | 10.0 | 57.0 |
| H. Alkaline lipase from strain Gr V-39 | | | | |
| STW | — | 6.2 | 91.6 | 97.9 |
| TPP | 2 | 15.5 | 53.3 | 68.8 |
| TPP | 10 | 57.4 | 9.3 | 66.7 |
| ALL-base | 2 | 28.6 | 16.8 | 45.3 |
| ALL-base | 4 | 25.7 | 14.4 | 40.1 |
| Liquid TIDE | 2 | 33.7 | 13.2 | 46.9 |

From these tables it clearly appears that the lipases of the present invention show their lipolytic properties on textile, and, in particular, their excellent performance in liquid and powder detergents under washing conditions.

EXAMPLE 10

This Example shows the compatibility of certain lipases of the present invention and bleach or a protein splitting enzyme under washing conditions. The performance of the lipases was tested by the SLM-method, as described on pages 18-19 of this specification under the following conditions:

ALL-base+bleach activator (TAED 3%): 4 g/l (pH 9.1).

ALL-base+TAED+bleach ($NaBO_3.4aq.$, 13%): 4 g/l (pH 9.1)

ALL-base+TAED+protease (2000 DU/g detergent): 4 g/l (pH 9.1)

The lipase activity units added (20 TLU) were obtained from the freeze-dried samples produced according to Example 2 and in the case of M1 to Example 3 (see Example 9).

Lipase strains: IN II-5, M1, Gr VI-15 and ATCC 29625.

Protease: MAXATASE. The proteolytic activity of MAXATASE (DU/l) was determined according to the Delft Method, described in J. Amer. Oil Chem. Soc. 60 (1983), 1672.

The results, expressed in the same way as in Example 9, are shown in the following tables:

| | Recovery (%) | | |
|---|---|---|---|
| Condition | Triglyceride | Free fatty acid | Total |
| A. Alkaline lipase from strain IN II-5 | | | |
| ALL-base + TAED | 4.4 | 62.4 | 66.8 |
| ALL-base + TAED + bleach | 5.7 | 64.5 | 70.2 |
| ALL-base + TAED + MAXATASE | 2.2 | 61.1 | 63.3 |
| B. Alkaline lipase from strain M-1 | | | |
| ALL-base + TAED | 35.1 | 16.1 | 51.2 |
| ALL-base + TAED + bleach | 38.1 | 14.9 | 53.0 |
| ALL-base + TAED + MAXATASE | 41.5 | 10.0 | 51.6 |
| C. Alkaline lipase from strain Gr VI-15 | | | |
| ALL-base + TAED | 42.0 | 7.4 | 49.4 |
| ALL-base + TAED + bleach | 43.2 | 7.5 | 50.7 |
| ALL-base + TAED + MAXATASE | 42.3 | 4.5 | 46.9 |
| D. Alkaline lipase from strain ATCC 29625 | | | |
| ALL-base + TAED | 34.7 | 19.8 | 54.5 |
| ALL-base + TAED + bleach | 32.6 | 27.5 | 60.1 |
| ALL-base + TAED + MAXATASE | 36.4 | 22.4 | 58.8 |
| E. Alkaline lipase from strain Thai IV 17-1 | | | |
| ALL-base + TAED | 31.0 | 17.2 | 48.2 |
| ALL-base + TAED + bleach | 32.9 | 13.8 | 46.7 |
| ALL-base + TAED + MAXATASE | 32.5 | 16.1 | 48.6 |

Also from these tables it clearly appears that the lipases of the present invention show their lipolytic properties on textile, and, in particular, their excellent performance in liquid and powder detergents under washing conditions.

We claim:

1. A biologically pure culture of *Pseudomonas pseudoalcaligenes* Sp 9, having the deposit accession number CBS 467.85.

2. A biologically pure culture of *Pseudomonas pseudoalcaligenes* IN II-5, having the deposit accession number CBS 468.85.

3. A biologically pure culture of *Pseudomonas pseudoalcaligenes* GR VI-15, having the deposit accession number CBS 471.85.

4. A biologically pure culture of *Pseudomonas pseudoalcaligenes* M-1, having the deposit accession number CBS 473.85.

* * * * *